United States Patent [19]

White et al.

[11] Patent Number: 4,532,081

[45] Date of Patent: Jul. 30, 1985

[54] SYNTHESIS OF 11-DEOXYPROSTAGLANDINS

[75] Inventors: William L. White, Holliston, Mass.; Peter B. Anzeveno, Zionsville, Ind.

[73] Assignee: The Dow Chemical Company, Midland, Mich.

[21] Appl. No.: 548,130

[22] Filed: Nov. 2, 1983

Related U.S. Application Data

[63] Continuation of Ser. No. 376,984, May 10, 1982, Pat. No. 4,447,636.

[51] Int. Cl.$^3$ ............................................. C07C 121/48
[52] U.S. Cl. ................................... 260/464; 560/121; 560/122
[58] Field of Search ................. 560/122, 121; 260/464

[56] References Cited

U.S. PATENT DOCUMENTS

| | | | |
|---|---|---|---|
| 3,828,026 | 8/1974 | Woodward | 424/246 X |
| 4,125,556 | 11/1978 | White et al. | 560/122 X |
| 4,146,553 | 3/1979 | Johnson | 260/464 |
| 4,447,636 | 5/1984 | White et al. | 560/122 |

OTHER PUBLICATIONS

Windholz, et al., Tetrahedron Letters, No. 27, pp. 2555–2557, (1967).

*Primary Examiner*—Joseph Paul Brust
*Attorney, Agent, or Firm*—Stephen L. Nesbitt; Gary D. Street; Ronald G. Brookens

[57] ABSTRACT

Improved procedures and intermediates for synthesizing 11-deoxyprostaglandins wherein trans-2,3-dicarbomethoxycyclopentanone is subjected to a novel alcoholysis with $\beta,\beta,\beta$-trichloroethanol to substitute a $\beta,\beta,\beta$2 -trichlorocarboethoxy group at the 2-position followed by alkylation to allow for a wide range of upper side chains to be introduced at the 2-position of the cyclopentanone ring. The unwanted $\beta,\beta,\beta$-trichlorocarboethoxy group at the 2-position can then be removed easily by a zinc induced elimination-decarboxylation sequence. Base catalyzed epimerization of the 2-position side chain to the desired trans-configuration, relative to the carbomethoxy group in the 3-position, is followed by partial reduction of the 2-hexynyl moiety of the side chain to the desired cis-olefinic group of the E$_2$-type 11-dioxyprostaglandins, or through total reduction to the alkane upper side chain of E$_1$-type-prostaglandin analogs. Modification thereafter of the carbonyl group at the 3-position of the cyclopentanone ring by a variety of reagents allows introduction of the lower side chain present in the prostaglandins themselves or a variety of other side chains derived from the 3-carboxy-, 3-hydroxymethyl- or 3-aldehyde-substituted cyclopentanone ring. From the latter, 11-deoxyprostaglandins can be prepared by known procedures.

1 Claim, No Drawings

SYNTHESIS OF 11-DEOXYPROSTAGLANDINS

CROSS-REFERENCE TO RELATED APPLICATION

This is a continuation of application Ser. No. 376,984, filed May 10, 1982, now U.S. Pat. No. 4,447,636.

SUMMARY OF THE INVENTION

This invention concerns improved methods and intermediates for synthesizing 11-deoxyprostaglandin precursors. In the new synthetic route, trans-2,3-dicarbomethoxycyclopentanone is subjected to a novel alcoholysis with $\beta,\beta,\beta$-trichloroethanol to substitute a 2-$\beta,\beta,\beta$-trichlorocarboethoxy group. Any required upper side chain thereafter can easily be introduced in its entirety in one step by an alkylation procedure. The unwanted $\beta,\beta,\beta$-trichlorocarboethoxy group at the 2-position of the resulting compound is readily removed by a zinc-induced elimination-decarboxylation sequence. Base catalyzed epimerization of the 2-position side chain to the desired trans-configuration, relative to the carbomethoxy group in the 3-position is followed by partial reduction of the 2-hexynyl moiety of the side chain to the desired cis-olefinic group of the $E_2$-type 11-deoxyprostaglandins, or by total reduction to the alkane upper side chain of $E_1$-type prostaglandin analogs. Thereafter, modification of the carbonyl group at the 3-position of the cyclopentanone ring, readily accomplished by a variety of reagents, allows introduction of the lower side chain present in the prostaglandins themselves or a variety of other side chains derived from the 3-carboxy-, the 3-hydroxymethyl- or the 3-aldehyde-substituted cyclopentanone ring. From the latter, 11-deoxyprostaglandins are readily synthesized by known procedures.

DESCRIPTION OF SOME PREFERRED EMBODIMENTS

The starting material used in the novel processes for making the intermediates for 11-deoxyprostaglandins is 1,2,4-tricarbomethoxybutane. This compound may be prepared by the procedure of U.S. Pat. No. 2,203,628 by nitric acid oxidation of a $\Delta^3$-cyclohexene which is substituted in at least one of the 1- and 2-positions of the cyclohexene nucleus by a carboxylic group. Thereafter, the resulting 1,2,4-tricarboxybutane is esterified to the trimethyl ester with methanol in the presence of an acidic catalyst, following well-known procedures. The series of reactions involved in the novel synthesis may be depicted by the following schematic representation:

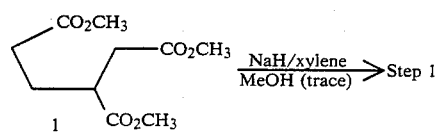

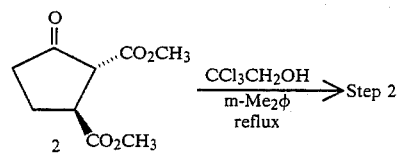

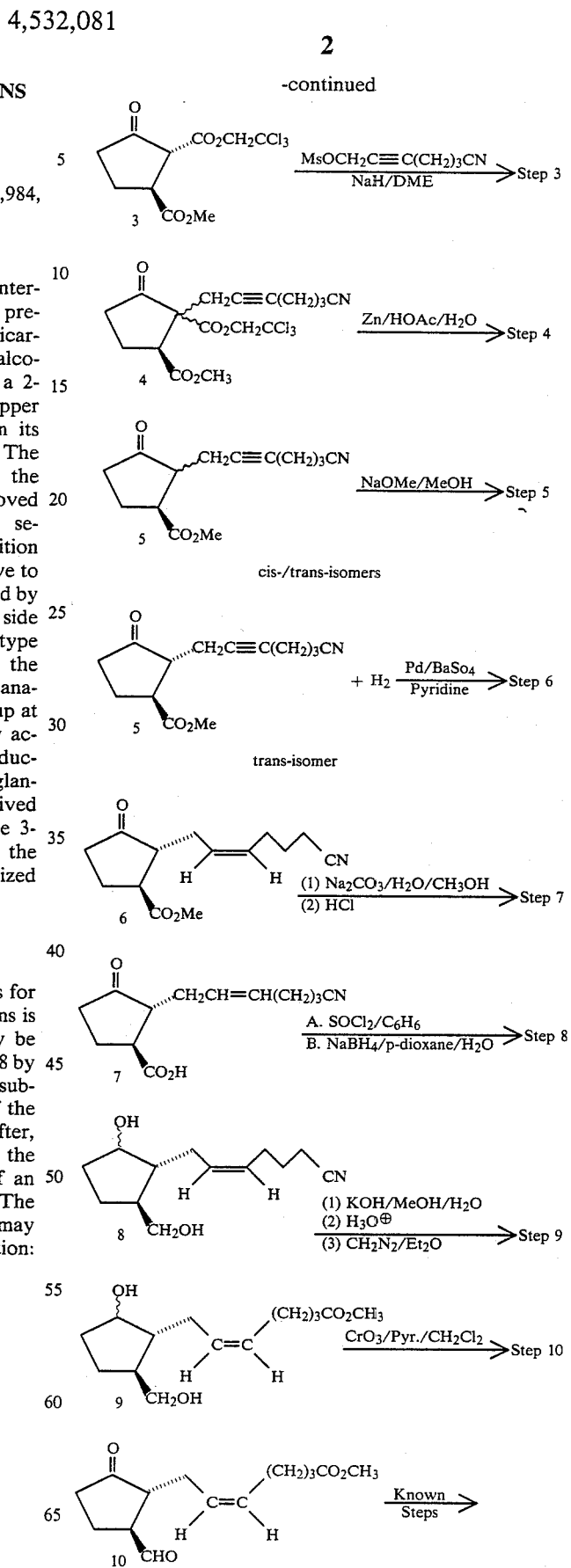

-continued

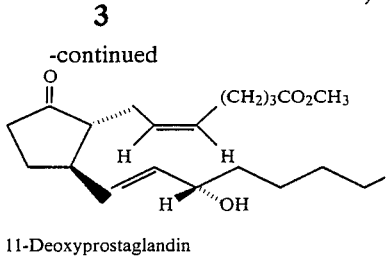

11-Deoxyprostaglandin

Step 1

If trans-2,3-dicarbomethoxycyclopentanone is not available, the first step in the synthetic scheme is the conversion of 1,2,4-tricarbomethoxybutane to trans-2,3-dicarbomethoxycyclopentanone. This is carried out by reacting the starting material with alkali metal hydride, used as a dispersion in mineral oil, the reaction medium being dry p-xylene in the presence of a trace of anhydrous methanol. The starting material is added stepwise to the reaction medium. The reaction temperature is maintained between about 20° C. and about 40° C. while the reaction mixture is stirred. Stirring is continued for a short time after addition of the starting material is complete, the resulting viscous mixture is diluted with water and the phases are separated. The aqueous phase is immediately acidified by addition thereto of citric acid monohydrate with stirring. The crude product is extracted several times, advantageously three times, with ethyl acetate and the combined organic phases are washed with water and twice with sodium chloride brine and dried over anhydrous magnesium sulfate. The solution is filtered, treated with decolorizing carbon, again filtered and concentrated in vacuo to give crude product which crystallizes upon seeding. This material, trans-2,3-dicarbomethoxycyclopentanone, 90–95% pure as determined by VPC, may be employed directly in the next step. Preferably, it should first be recrystallized from ethyl ether/petroleum ether.

Most prior art procedures for making the product of the first step have given a mixture of the first step product and it isomeric cyclization product, 2,4-dicarbomethoxycyclopentanone. By the procedure of U.S. Pat. No. 4,146,553 just described, virtually none of the unwanted 2,4-isomer (<10%) is produced.

Step 2

In this step, alcoholysis with $\beta,\beta,\beta$-trichloroethanol provides a trichlorocarboethoxy group in place of the carbomethoxy group at the 2-position prior to the introduction at the 2-position of a required side chain. This is accomplished by stirring a mixture of 2,3-dicarbomethoxycyclopentanone with excess $\beta,\beta,\beta$-trichloroethanol in refluxing m-xylene with provision for intermittent removal of solvent. Following a total reaction time of ca. 115 hours, the solution is concentrated and the residual oil is triturated with ligroin. The resulting solid is taken up in boiling aqueous methanol, treated with decolorizing carbon and filtered. Trans-2-$\beta,\beta,\beta$-trichlorocarboethoxy-3-carbomethoxycyclopentanone, a new compound, crystallizes out.

Step 3

In this step, position 2 is alkylated to introduce a required side chain. The side chain is introduced in its entirety in one step. Thereby, a wider range of side chains can be introduced than has heretofore been possible. The introduction of the desired side chain via a nucleophilic displacement utilizes any compound $NC(CH_2)_3C\equiv CCH_2X$ in which X is a good leaving group. Thus, to a mechanically stirred suspension of a mineral oil dispersion of sodium hydride in dry dimethoxyethane is added during 30 minutes a solution of a substantially equimolar proportion of trans-2-$\beta,\beta,\beta$-trichlorocarboethoxy-3-carbomethoxy cyclopentanone in dry dimethoxyethane. Stirring is continued for ca. one and one-half hours after addition is complete, during which hydrogen evolution ceases. A solution of a substantially equimolar proportion of the methane sulfonate of 6-cyano-2-hexyne-1-ol in dry dimethoxyethane is added during ca. 10 minutes. The resulting light tan mixture is heated at reflux for ca. 24 hours, cooled, diluted with 100 ml of water and exhaustively extracted with ethyl acetate. The combined extracts are washed several times with NaCl brine and dried over anhydrous magnesium sulfate. The filtered solution is concentrated in vacuo to afford, (after washing by decantation several times with hexane and removal of residual solvent at the stripper) a 96% yield of crude product. Purification is accomplished via chromatography on silica gel, using benzene/ethyl acetate, (95/5), as solvent. The pure product, (72% yield, typically) is obtained as a viscous, colorless oil.

Other alkylating agents which can be used include compounds having the formula $NC(CH_2)_3C\equiv CCH_2X$ in which X is bromo, chloro, iodo or p-tolylsulfonyl; $Br(CH_2)_6CO_2CH_3$, $Br(CH_2)_6CN$ and $BrCH_2C\equiv CCH_2CH_3$. Broadly, the following alkylating agents are useful in the alkylation:

cis-$XCH_2CH=CH(CH_2)_3CN$,
$X(CH_2)_3(CH_2)_xCN$,
$XCH_2C\equiv C-CH_2Si(CH_3)_2CH_2CN$,
$XCH_2C\equiv CCH_2SCH_2CN$,
$XCH_2C\equiv C(CH_2)_3CO_2R$,
$XCH_2C\equiv CCH_2N(CH_3)CH_2CN$,
$XCH_2C\equiv CCH_2OCH_2CN$,
$XCH_2C\equiv C(CH_2)_xCN$,
$XCH_2C\equiv C(CH_2)_3SO_2NHCH_3$,
cis-$XCH_2CH=CHCH_2SCH_2CN$,
$XCH_2C\equiv CCH_2C(CH_3)_2CH_2CN$ and
$XCH_2C\equiv CCH_2N(CH_2CN)_2$, wherein X is a good leaving group and x is 1 to 10 ($\neq 3$).

The product of Step 3 is a new compound.

Step 4

In Step 4, the unwanted $\beta,\beta,\beta$-trichlorocarboethoxy group at the 2-position of the cyclopentanone moiety is readily removed by hydrogenolysis with zinc dust in aqueous acetic acid at room temperature for 3.5 hours. After filtering with suction, the removed solids are washed with several small portions of glacial acetic acid, the combined filtrate and washings are concentrated and the residue is partitioned between ethyl acetate and water. After washing the organic phase with sodium bicarbonate and sodium chloride solutions, the dried solution is concentrated in vacuo to produce a 1:1 mixture of cis:trans-isomers of the product, 2-(6'-cyano-2'-hexynyl)-3-carbomethoxycyclopentanone.

Step 5

The cis:trans-isomer mixture from Step 4 is epimerized to the required all trans-isomer with a catalytic amount of sodium methoxide in methanol at room temperature. Following acidification with glacial acetic acid, the mixture is concentrated in vacuo and the residue is taken up in ethyl acetate and washed with sodium bicarbonate and sodium chloride solutions. The dried solution is then concentrated in vacuo to provide trans-2-(6'-cyano-2'-hexynyl)-3-carbomethoxycyclopentanone.

Step 6

The compound of Step 5 is catalytically selectively hydrogenated using 5% palladium on barium sulfate in pyridine at 25° C. and one atmosphere pressure until one mole of hydrogen has been consumed. After removal of the catalyst, most of the pyridine is removed in vacuo and the residue is taken up in ethyl acetate and washed with dilute hydrochloric acid and sodium chloride solutions and dried. The filtered solution is concentrated in vacuo and the crude product is purified via silica gel chromatography using benzene/ethyl acetate, (93/7), as solvent. The pure product, (95% yield), of trans-2-(6'-cyano-cis-2'-hexenyl)-3-carbomethoxycyclopentanone, is obtained as a colorless oil.

Step 7

In Step 7, the carbomethoxy group in the 3-position on the cyclopentanone nucleus is saponified with aqueous methanolic sodium carbonate at about 75° C. to give, upon acidification with concentrated hydrochloric acid, the compound 7 having a carboxylic acid group in the 3-position. The reaction is a known type reaction.

Step 8

In Step 8A, compound 7 is transformed to its acid chloride by reaction with thionyl chloride in dry benzene under anhydrous conditions at about 85°–90° C. and, after recovery, is employed immediately in the following step.

In Step 8B, the diol is prepared from the preceding acid chloride by reduction with alkali metal borohydride in p-dioxane/water in a conventional reduction at about 0° to 5° C. to give the compound trans-2-(6'-cyano-cis-2'-hexenyl)-3-hydroxymethylcyclopentanol.

Step 9

In Step 9, the 6'-cyano-cis-2'-hexenyl group in position 2 is transformed to the corresponding 6'-carbomethoxy-cis-2'-hexenyl compound by hydrolyzing the cyano moiety to carboxylate with aqueous methanolic alkali metal hydroxide, liberating the acid from the resulting carboxylate salt with concentrated mineral acid, and treating the latter with diazomethane to give product 9, trans-2-(6'-carbomethoxy-cis-2'-hexenyl)-3-hydroxymethylcyclopentanol as a viscous oil.

Step 10

In final Step 10, compound 9 is selectively oxidized by adding a solution of it in a non-reactive solvent, advantageously methylene chloride, to a solution of anhydrous chromium trioxide in a mixture of about two molar proportions of anhydrous pyridine in dry methylene chloride. The reaction is carried out at about 25° C. At the completion of the reaction, compound 10, trans-2-(6'-carbomethoxy-cis-2'-hexenyl)-3-formylcyclopentanone is recovered. As is well known to art-skilled persons, this compound is readily transformed to 11-deoxyprostaglandins via known steps.

The following examples describe completely representative specific embodiments of the invention and the best mode contemplated by the inventors of carrying out the invention.

EXAMPLE 1

Trans-2,3-dicarbomethoxycyclopentanone, 2

To a mechanically-stirred suspension of 30.5 g, 0.72 mole, of a 57 percent mineral oil dispersion of sodium hydride in 450 ml of dry p-xylene was added 20 ml of a solution of 142.5 g, 0.60 mole, of 1,2,4-tricarbomethoxybutane in 125 ml of dry p-xylene and 1 ml of anhydrous methanol. After the reaction had commenced, the remainder of the ester solution was added at 20°–25° C. during 1.5 hours. Stirring was continued for 20 minutes after addition was complete, the viscous mixture was diluted with 200 ml of water and the phases were separated. The aqueous phase was immediately acidified by addition of a stirred solution of 45.0 g, 0.21 mole, of citric acid monohydrate in 125 ml of water. The crude product was extracted into three 250 ml portions of ethyl acetate and the combined organic phases were washed with 100 ml of water and with two 100 ml portions of sodium chloride brine and dried over anhydrous magnesium sulfate. The filtered solution was treated with 7.0 g of decolorizing carbon, filtered again and concentrated in vacuo to afford 90.0 g, 75 percent, of crude product which crystallized upon seeding. This material, which is 90–95 percent pure titular compound via VPC, when recrystallized from ether/petroleum ether (30°–60° C.), was obtained as colorless needles, m.p. 49.0°–50.0° C.

Anal. Calc. for $C_9H_{12}O_5$: C, 53.99; H, 6.04. Found: C, 53.92; H, 6.01.

The 2,4-dinitrophenylhydrazone thereof was obtained as golden felted needles, m.p. 145.0°–146.5° C., from methanol.

Anal. Calc. for $C_{15}H_{16}N_4O_8$: C, 47.37; H, 4.24; N, 14.73. Found: C, 47.41; H, 4.24; N, 14.71.

EXAMPLE 2

Trans-2-$\beta,\beta,\beta$-trichlorocarboethoxy-3-carbomethoxycyclopentanone, 3

A magnetically stirred solution of 35.0 g, 0.175 mole, of trans-2,3-dicarbomethoxycyclopentanone and 90.0 g, 0.602 mole, of $\beta,\beta,\beta$-trichloroethanol in 700 ml of dry m-xylene was heated at reflux with provision for intermittent removal of solvent according to the following schedule, (the progress of the reaction may be conveniently followed by silica gel TLC utilizing benzene/methanol, (95/5), as solvent.

| Time | Distillate, ml | Head Temp., °C. |
| --- | --- | --- |
| 1.5 hr. | 20 | 128 |
| Reflux, 48 hr. | | |
| 1.0 hr. | 70 | 136 |
| Reflux, 24 hr. | | |
| 2.5 hr. | 410 | 140 |

An additional 15.0 g, 0.100 mole, of $\beta,\beta,\beta$-trichloroethanol was then added and reflux was continued for forty-three hours. The brown mixture was then concentrated at the stripper and, while chilling in an ice/salt bath, was triturated with ligroin. The resulting crude solid was filtered, washed well with cold ligroin and recrystallized from methanol/water, (Norite), as colorless, felted needles, m.p. 81.0°–83.0° C. The yield of titular product was 36.0 g, (64%).

Anal. Calc. for $C_{10}H_{11}Cl_3O_5$: C, 37.82; H, 3.40; Cl, 33.49. Found: C, 37.83; H. 3.60; Cl, 33.43.

The 2,4-dinitrophenylhydrazone thereof was obtained as golden felted needles, m. pt. 103.5°–105.0° C. from methanol.

Anal. Calc. for $C_{16}H_{15}Cl_3N_4O_8$: C, 38.41; H, 3.04; N, 11.02. Found: C, 38.61; H. 2.94; N, 11.23.

Concentration of the mother liquors and recrystallization of the residue afforded an additional 5.1 g, (9% yield), of slightly less pure product, m.p. 79.0°–83.0° C.

EXAMPLE 3

2-(6'-Cyano-2'-hexynyl)-2-β,β,β-trichlorocarboethoxy-3-carbomethoxycyclopentanone, 4

To a mechanically stirred suspension of 4.80 g, 0.100 mole, of a 50 percent mineral oil dispersion of sodium hydride in 100 ml of dry dimethoxyethane was added during 30 minutes a warm solution of 31.80 g, 0.100 mole, of trans-2-β,β,β-trichlorocarboethoxy-3-carbomethoxycyclopentanone in 150 ml of dry dimethoxyethane. Stirring was continued for 1 hour after addition was completed, during which time hydrogen evolution ceased. A solution of 20.10 g, 0.100 mole, of the methane sulfonate of 6-cyano-2-hexyne-1-ol in 20 ml of dry dimethoxyethane was added during 10 minutes while the mixture was gradually warmed to reflux. The stirred mixture was heated at reflux for 24 hours, cooled, diluted with 100 ml of water and exhaustively extracted with ethyl acetate. The combined extracts were washed with 3×75 ml of brine and were dried over anhydrous magnesium sulfate. The filtered solution was concentrated in vacuo to afford, (after washing by decantation with 3×30 ml of hexane and removal of residual solvent at the stripper), 40.8 g, (96% yield), of oily product. Purification was accomplished via chromatography on 500 g of silica gel, using benzene/ethyl acetate, (95/5), as solvent. The pure titular product, (30.5 g, 72% yield), was obtained as a viscous, faint yellow oil, shown by H'-NMR to exist as a 1:1 mixture of cis:trans-isomers.

I.R.: 2240 (w, —C≡C—, and/or —CN), 1765 (vs, >C=O, ketone) and 1735 cm.$^{-1}$, (vs, >C=O, ester).

H'-NMR: δ=1.80 (m, 2H, side chain, —C—CH$_2$—C—), 2.83 (m, broad, 11H, ring, —CH$_2$CH$_2$CH— and side chain, —CH$_2$C≡CCH$_2$CCH$_2$CN), 3.72 (s, 3H, —OCH$_3$), 4.60 and 4.70, (2 singlets, cis:trans-isomers, 2H, —OCH$_2$CCl$_3$).

Anal. Calc'd. for $C_{17}H_{18}Cl_3NO_5$: C, 48.30; H, 4.29; N, 3.31; Cl, 25.16. Found: C, 48.42; H, 4.48; N, 3.59; Cl, 24.92.

EXAMPLE 4

Trans-2-(6'-cyano-2'-hexynyl)-3-carbomethoxycyclopentanone, 5

(A) Preparation of the cis-/trans-isomers, 5;

A magnetically stirred suspension of 23.0 g of freshly activated zinc dust in 300 ml of 90 percent aqueous acetic acid containing 25.0 g, 0.06 mole, of the alkylated cyclopentanone 4 was filtered at the pump after 3.5 hours. The residual zinc was washed with several small portions of glacial acetic acid and the combined filtrates were concentrated at the stripper. The residual oil was taken up in 125 ml of ethyl acetate, washed with 2×30 ml of 5 percent aqueous sodium bicarbonate solution and with 3×50 ml of brine and finally dried over anhydrous magnesium sulfate. Filtration and concentration at the stripper afforded 14.0 g, (95% yield), of pure product, shown by H'-NMR to be a 1:1 mixture of cis-/trans-isomers, 5.

(B) Isomerization to the trans-isomer, 5

The 14.0 g of product obtained in (A) above was magnetically stirred under anhydrous conditions with 150 ml of dry methanol containing a pea-sized piece of clean sodium metal for eighty-eight hours. The resulting orange solution was then quenched with 1.5 ml of glacial acetic acid and concentrated at the stripper. The resulting residual oil was taken up in 100 ml of ethyl acetate, washed with 2×30 ml of 5 percent aqueous sodium bicarbonate solution and with 3×30 ml of brine and dried over anhydrous magnesium sulfate. Filtration and concentration at the stripper afforded 13.3 g, (95% yield), of pure titular product as a faint yellow oil, shown via H'-NMR to be ≃95 percent trans-isomer, 5.

EXAMPLE 5

Trans-2-(6'-cyano-cis-2'-hexenyl)-3-carbomethoxycyclopentanone, 6

To a magnetically stirred solution of 12.8 g, 0.052 mole, of trans-2-(6'-cyano-2'-hexynyl)-3-carbomethoxycyclopentanone in 150 ml of reagent grade pyridine was added 2.0 g of 5% palladium on barium sulfate and the mixture was hydrogenated at one atmosphere hydrogen pressure and 25° C. After 60 minutes, the theoretical amount of hydrogen, (1,185 ml), was consumed, and the reaction was terminated. The catalyst was removed by vacuum filtration through a celite pad and washed with several small portions of ethyl acetate. The combined filtrates were concentrated at the stripper and, after cooling, the residual oil was taken up in 150 ml of ethyl acetate and washed with 3×60 ml of 1-normal hydrochloric acid and with 3×75 ml of brine. Drying (MgSO$_4$), vacuum filtration and concentration at the stripper afforded 12.8 g of a somewhat viscous, faint yellow oil. Chromatography on 150 g of silica gel using benzene:ethyl acetate (93/7) as eluant provided 12.1 g, (95% yield) of pure trans-2-(6'-cyano-2'-cis-hexenyl)-3-carbomethoxycyclopentanone as a colorless oil.

I. R.: 2240 (w, —CN) and 1740 cm.$^{-1}$ (vs, >C=O, ketone and ester).

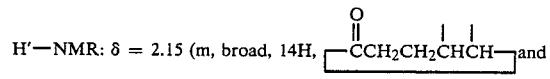

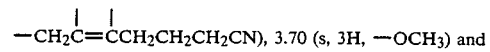

—CH$_2$C=CCH$_2$CH$_2$CN), 3.70 (s, 3H, —OCH$_3$) and

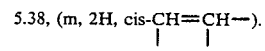

Anal. Calc'd. for $C_{14}H_{19}NO_3$: C, 67.44; H, 7.68; N, 5.62. Found: C, 67.34; H, 7.65; N, 5.50.

EXAMPLE 6

Trans-2-(6'-cyano-cis-2'-hexenyl)-3-carboxycyclopentanone, 7

A magnetically stirred mixture of 15.00 g, 0.061 mole, of trans-2-(6'-cyano-2'-cis-hexenyl)-3-carbomethoxycyclopentanone in 150 ml of 5 percent aqueous sodium carbonate solution and 25 ml of methanol was warmed in an oil bath at 75°–80° C. under a slight positive nitrogen pressure for 4 hours, cooled, and stirred at 25° C. overnight. The resulting solution was washed with three 25 ml portions of ethyl acetate and while chilling in an ice bath was acidified with concentrated hydrochloric acid. The yellow oil which separated was extracted into three 50 ml portions of ethyl acetate and the combined extracts were washed with three 30 ml portions of brine and were dried over anhydrous magnesium sulfate. Filtration and concentration in vacuo afforded 12.6 g, (89 percent), of crude acid as a viscous yellow oil. This material may be utilized directly in the following step.

EXAMPLE 7

Trans-2-(6'-cyano-cis-2'-hexenyl)-3-hydroxymethylcyclopentanol, 8

(A) Preparation of the Acid Chloride:

A magnetically stirred solution of 7.00 g 0.030 mole, of trans-2-(6'-cyano-cis-2'-hexenyl)-3-carboxycyclopentanone and 6.85 g, 0.058 mole, of freshly distilled thionyl chloride in 175 ml of dry benzene was heated under anhydrous conditions in an oil bath at 85°-90° C. for 3 hours, cooled and concentrated in vacuo. An additional 25 ml of dry benzene was added and again the solution was concentrated in vacuo. After storing at 0.1 mm for 2 hours, the quantitative yield of crude yellow-brown acid chloride was fully characterized by its IR and H'-NMR spectra and was employed immediately in the next step.

(B) Preparation of the Diol, 8:

To a chilled, magnetically stirred suspension of 1.40 g, 0.037 mole, of sodium borohydride in 40 ml of p-dioxane and 40 ml of water was added during 30 minutes at 0°-5° C. a solution of all of the acid chloride obtained in (A) above, in 40 ml of p-dioxane. After addition was complete, 0.40 g, 0.010 mole, of sodium borohydride was added cautiously and the foaming mixture was stirred at 0°-5° C. for 1 hour, after which 0.20 g 0.005 mole, of sodium borohydride was added in one portion and stirring at 0°-5° C. was continued for 45 minutes. The cooling bath was then removed and the stirred mixture was warmed during 15 minutes to 25° C. and poured into 100 ml of brine. After exhaustive extraction with ethyl acetate, the combined extracts were washed with 75 ml of brine, with two 50 ml portions of 10 percent aqueous sodium bicarbonate solution and with two 50 ml portions of brine and were dried over anhydrous magnesium sulfate. The filtered solution was concentrated in vacuo to afford 6.0 g, (96% yield), of crude titular diol which was fully characterized by its IR and H'-NMR spectra and was employed directly in the next step.

EXAMPLE 8

Trans-2-(6'-carbomethoxy-cis-2'-hexenyl)-3-hydroxymethylcyclopentanol, 9

A magnetically stirred suspension of 4.00 g, 0.018 mole, of trans-2-(6'-cyano-cis-2'-hexenyl)-3-hydroxymethylcyclopentanol in a solution of 7.00 g, 0.124 mole, of potassium hydroxide in 50 ml of water and 5 ml of methanol was heated at reflux for 1 hour, during which time the substrate dissolved. After cooling and backwashing with three 25 ml portions of ether the yellow basic solution was treated with decolorizing carbon, chilled, and acidified with concentrated hydrochloric acid and extracted into three 25 ml portions of ethyl acetate. The combined extracts were washed with two 25 ml portions of brine, dried over anhydrous magnesium sulfate, filtered and concentrated in vacuo to afford 4.00 g, (93% yield), of crude acid product as a viscous, colorless oil.

A magnetically stirred solution of 3.10 g, 0.013 mole, of the crude acid in 20 ml of ether and 5 ml of methanol was treated with a slight excess of ethereal diazomethane to a persistent faint yellow color and stirred at 25° C. for 1 hour. The excess diazomethane was quenched by the dropwise addition of glacial acetic acid, and the resulting solution was diluted with 25 ml of ether, washed with two 15 ml portions of 5 percent aqueous sodium bicarbonate solution, and with two 10 ml portions of brine and dried over anhydrous magnesium sulfate. The filtered solution was concentrated in vacuo to afford 3.15 g, (96% yield), of the titular carbomethoxy diol as a viscous colorless oil which on the basis of its spectroscopic and silica gel TLC characterization, was employed directly in the final step.

EXAMPLE 9

Trans-2-(6'-carbomethoxy-cis-2'-hexenyl)-3-formylcyclopentanone, 10

To a mechanically stirred, chilled solution of 9.84 g, 0.12440 mole of anhydrous pyridine in 150 ml of dry methylene chloride was added in several portions during 15 seconds 6.320 g, 0.06220 mole, of anhydrous chromium trioxide. The cooling bath was removed and the resulting deep burgundy solution was stirred under dry nitrogen for 15 minutes. A solution of 1.328 g, 0.00518 mole of trans-2-(6'-carbomethoxy-cis-2'-hexenyl)-3-hydroxy-methylcyclopentanol in 3 ml of dry methylene chloride was added in one portion, washed in with an additional 1 ml of solvent and the resulting black tarry mixture was stirred at 25° C. for 20 minutes. The dark solution was decanted from the residue, which was washed with two 100 ml portions of ether and the combined organic phases were washed with three 100 ml portions of 5 percent aqueous sodium hydroxide, with 100 ml of 5 percent aqueous hydrochloric acid, with 100 ml of 5 percent aqueous sodium bicarbonate and finally with two 100 ml portions of brine. After drying with anhydrous magnesium sulfate, the filtered solution was concentrated in vacuo to afford 1.240 g of crude product which was chromatographed on 20.0 g of silica gel using benzene/acetone, (98/2) as eluent. The titular product keto-aldehyde, 1.195 g, (92% yield), was obtained as a colorless, mobile oil which was pure by TLC and by IR, H'-NMR and mass spectrometry and which may be employed directly in subsequent work in known ways to prepare 11-deoxyprostaglandins.

What is claimed is:

1. 2-(6'-cyano-2'-hexynyl)-2-$\beta,\beta,\beta$-trichlorocarboethoxy-3-carbomethoxy cyclopentanone.

* * * * *